United States Patent
Tapper et al.

(10) Patent No.: US 11,406,842 B2
(45) Date of Patent: Aug. 9, 2022

(54) GARMENT INCLUDING THERAPEUTIC LIGHT SOURCE

(71) Applicant: Purple Haze LLC, Wayne, PA (US)

(72) Inventors: Jay Tapper, Wayne, PA (US); Jens Johnson, Austin, TX (US); Lawrence A. Blaustein, Chagrin Falls, OH (US); Jaleh Factor, Manhattan Beach, CA (US)

(73) Assignee: BIOTHREAD LLC, Wayne, PA (US)

( * ) Notice: Subject to any disclaimer, the term of this patent is extended or adjusted under 35 U.S.C. 154(b) by 1020 days.

(21) Appl. No.: 16/005,946

(22) Filed: Jun. 12, 2018

(65) Prior Publication Data

US 2019/0374792 A1 Dec. 12, 2019

(51) Int. Cl.
*A61N 5/06* (2006.01)
*A41D 1/00* (2018.01)
(Continued)

(52) U.S. Cl.
CPC ............ *A61N 5/0616* (2013.01); *A41D 1/002* (2013.01); *A41D 13/1236* (2013.01); *A61N 5/0622* (2013.01); *D02G 3/441* (2013.01); *G02B 6/001* (2013.01); *A41B 11/00* (2013.01); *A41B 2400/32* (2013.01); *A41D 2400/32* (2013.01);
(Continued)

(58) Field of Classification Search
CPC .............. A61N 5/0616; A61N 5/0622; A61N 2005/0659; A61N 2005/0662; A61N 2005/063; A61N 2005/0645; A61N 2005/0658; A61N 2005/0665; A41D 13/1236; A41D 1/002; A41D 2400/32; A41D 27/085; A41D 2400/28;
(Continued)

(56) References Cited

U.S. PATENT DOCUMENTS 4,234,907 A * 11/1980 Daniel .................. D02G 3/441
362/556
4,727,603 A 3/1988 Howard
(Continued)

FOREIGN PATENT DOCUMENTS

CN 205267047 6/2016
DE 102008018805 A1 * 10/2009 ............. G02B 6/001
(Continued)

OTHER PUBLICATIONS

Furukawa Review No. 45, 2014, "Bend insensitive Single-Mode Optical Fiber" 50-52 (Year: 2014).*
(Continued)

*Primary Examiner* — Brian T Gedeon
*Assistant Examiner* — Joshua Andrew Schum-Houck
(74) *Attorney, Agent, or Firm* — Rankin, Hill & Clark LLP

(57) ABSTRACT

A garment includes a fabric base layer and at least one side-emitting optical fiber retained to or integrated with the fabric base layer. The fabric base layer can stretch in the grain and cross grain direction of the fabric base layer. The at least one side-emitting optical fiber is located in at least one light-emitting zone to be located over a targeted body area of the person wearing the garment, and is configured to receive light from a light source and in the at least one light-emitting zone is configured to project light having a therapeutic wavelength toward the targeted body area.

83 Claims, 6 Drawing Sheets

(51) Int. Cl.
*D02G 3/44* (2006.01)
*F21V 8/00* (2006.01)
*A41D 13/12* (2006.01)
*A41B 11/00* (2006.01)

(52) U.S. Cl.
CPC .............. *A61N 2005/063* (2013.01); *A61N 2005/0645* (2013.01); *A61N 2005/0658* (2013.01); *A61N 2005/0659* (2013.01); *A61N 2005/0662* (2013.01); *A61N 2005/0665* (2013.01); *D10B 2401/20* (2013.01)

(58) Field of Classification Search
CPC ........ D02G 3/441; G02B 6/001; A41B 11/00; A41B 2400/32; D10B 2401/20
See application file for complete search history.

(56) References Cited

U.S. PATENT DOCUMENTS

| | | | |
|---|---|---|---|
| 4,761,047 A | 8/1988 | Mori | |
| 6,341,504 B1 | 1/2002 | Istook | |
| 8,214,008 B2 | 7/2012 | Hassonjee et al. | |
| 8,428,686 B2 | 4/2013 | Kuo et al. | |
| 8,709,185 B2 * | 4/2014 | Hassonjee | B32B 5/26 156/179 |
| 9,335,457 B2 * | 5/2016 | Zimmermann | D03D 11/00 |
| 2002/0138120 A1 | 9/2002 | Whitehurst | |
| 2003/0167080 A1 | 9/2003 | Hart et al. | |
| 2004/0204639 A1 | 10/2004 | Casciani | |
| 2005/0109418 A1 * | 5/2005 | Liao | D03D 15/56 139/420 R |
| 2006/0087832 A1 * | 4/2006 | Peng | D03D 15/54 362/103 |
| 2007/0288071 A1 * | 12/2007 | Rogers | A61N 5/062 607/88 |
| 2008/0221488 A1 * | 9/2008 | Kurono | A61B 5/113 600/595 |
| 2010/0114263 A1 * | 5/2010 | Pressler | A61N 5/0621 607/88 |
| 2010/0249557 A1 | 9/2010 | Besko | |
| 2014/0070957 A1 | 3/2014 | Longinotti-Buitoni et al. | |
| 2014/0074010 A1 * | 3/2014 | Veres | A61N 5/062 604/20 |
| 2014/0303693 A1 | 10/2014 | Haarlander et al. | |
| 2016/0121136 A1 * | 5/2016 | Tao | A61N 5/0621 607/89 |
| 2016/0122907 A1 * | 5/2016 | Liu | D03D 15/56 442/200 |
| 2016/0265146 A1 * | 9/2016 | Liao | D04B 15/80 |
| 2017/0045703 A1 * | 2/2017 | Pitwon | G02B 6/38 |
| 2017/0342607 A1 | 11/2017 | Yamada | |

FOREIGN PATENT DOCUMENTS

| | | |
|---|---|---|
| WO | 2011/082420 | 7/2011 |
| WO | 2014071898 | 5/2014 |
| WO | 2017/120367 | 7/2017 |

OTHER PUBLICATIONS

International Search Report filed in PCT/US2019/036223 dated Aug. 28, 2019.

* cited by examiner

GARMENT INCLUDING THERAPEUTIC LIGHT SOURCE

BACKGROUND

Clothing made from light emitting fabrics is described in U.S. Pat. No. 4,234,907. This patent, however, describes such clothing as a fad item or as safety clothing to emit light outward when the wearer wishes to be seen.

US 2007/0089800A1 discloses garment systems that include an integrated infrastructure for monitoring vital signs of an individual and for other monitoring purposes. Neither of the aforementioned patent documents discloses a garment for delivering light of a therapeutic wavelength toward a wearer of the garment.

SUMMARY

In view of the foregoing, a garment includes a fabric base layer and at least one side-emitting optical fiber retained to or integrated with the fabric base layer. The fabric base layer has at least 8% stretch in the grain and cross grain direction of the fabric base layer. The at least one side-emitting optical fiber is located in at least one light-emitting zone to be located over a targeted body area of the person wearing the garment, and is configured to receive light from a light source and in the at least one light-emitting zone is configured to project light having a therapeutic wavelength toward the targeted body area.

Another example of a garment includes a knitted fabric base layer and at least one side-emitting optical fiber retained to or integrated with the fabric base layer. The at least one side-emitting optical fiber is located in at least one light-emitting zone to be located over a targeted body area of the person wearing the garment, and is configured to receive light from a light source and in the at least one light-emitting zone is configured to project light having a therapeutic wavelength toward the targeted body area.

A garment for delivering light therapy has a dual or multiple layer construction in an area covering a targeted body area of a person wearing the garment. In the area of the dual or multiple layer construction, at least one side-emitting optical fiber is configured to be optically connected with a light source to deliver therapeutic light to the targeted body area.

Another example of a garment is a therapeutic sock including a fabric base layer and at least one side-emitting optical fiber retained to or integrated with the fabric base layer. The fabric base layer includes an elastic fiber in at least an elastic portion of the sock. The elastic portion has at least 8% stretch in at least one of the grain and cross grain direction. The at least one side-emitting optical fiber is located in at least one light-emitting zone to be located over a targeted body area of the person wearing the sock. The at least one side-emitting optical fiber is configured to receive light from a light source and in the at least one light-emitting zone is configured to project light having a therapeutic wavelength toward the targeted body area.

Another example of a garment includes a fabric base layer and at least one side-emitting optical fiber retained to or integrated with the fabric base layer. The fabric base layer is configured to conform to the person's skin when wearing the garment and retains the at least one side-emitting optical fiber adjacent to or in contact with the person's skin when wearing the garment. The at least one side-emitting optical fiber is located in at least one light-emitting zone to be located over a targeted body area of the person wearing the garment. The at least one side-emitting optical fiber is configured to receive light from a light source and in the at least one light-emitting zone is configured to project light having a therapeutic wavelength toward the targeted body area. The at least one light-emitting zone is adjustable when the person is wearing the garment to modify a position of the at least one light-emitting zone with respect to the targeted body area of the person wearing the garment and maintain contact with the person's skin while the person wearing the garment is moving.

DETAILED DESCRIPTION

Figure 1:
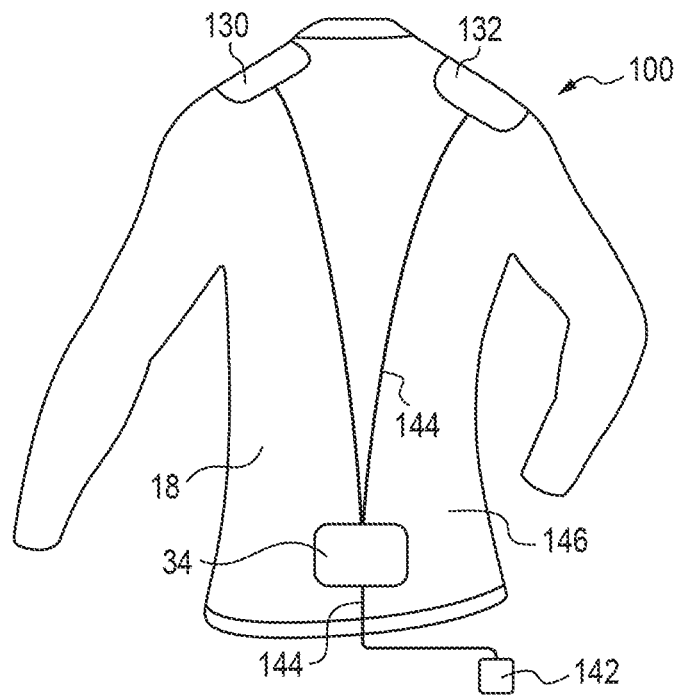
FIG. 1 is a schematic depiction of a rear of a garment configured to deliver therapeutic light toward a wearer of the garment.
Figure 2:
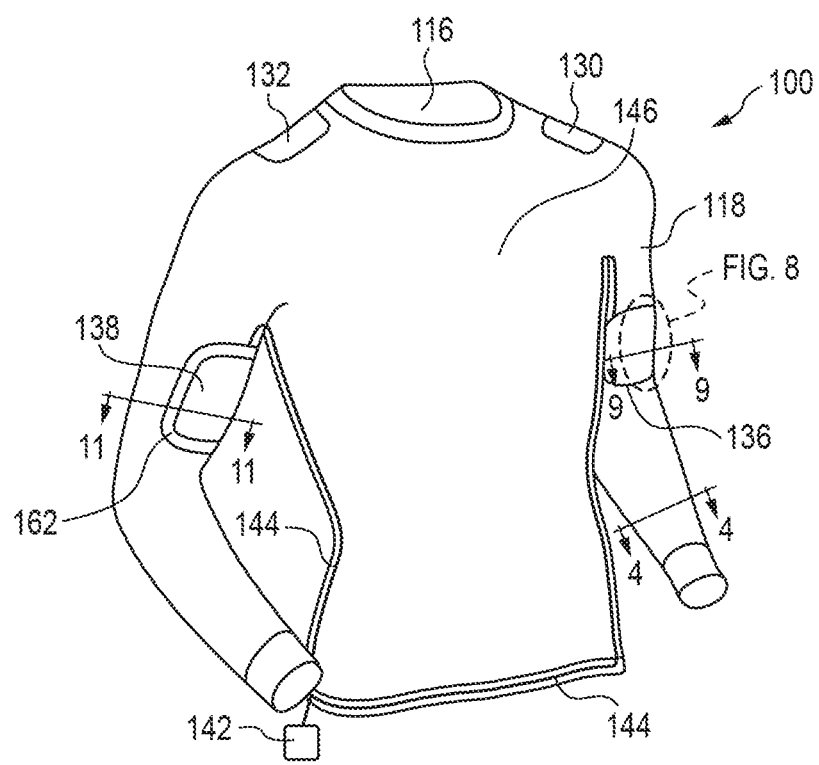
FIG. 2 is a schematic depiction of a front of the garment depicted in FIG. 1.
Figure 3:
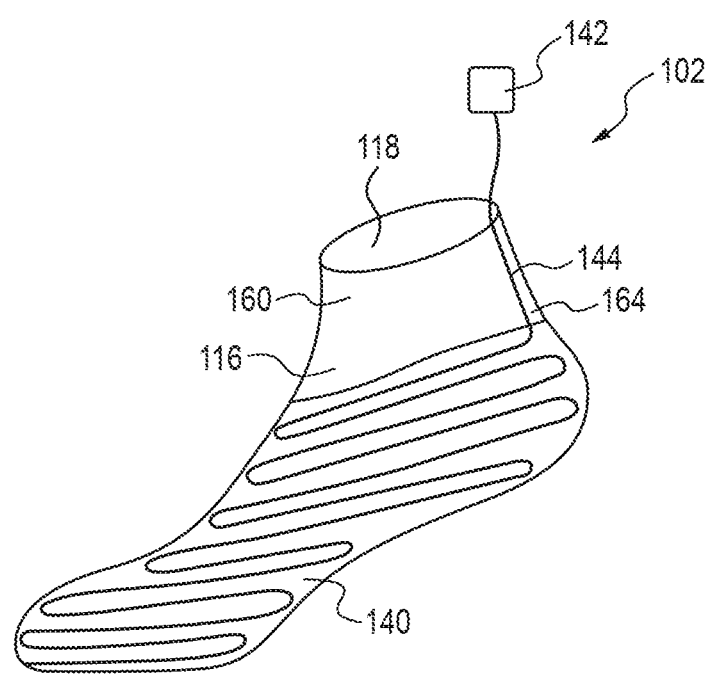
FIG. 3 is a schematic depiction of another garment configured to deliver therapeutic light toward a wearer of the garment

FIGS. 1 and 2 depict a garment 100 and FIG. 3 depicts another garment 102 that are each configured to project light having a therapeutic wavelength toward a targeted body area of a person wearing the garment 100. For example, light having a wavelength between 630 nm and 900 nm has been found beneficial to increase blood flow, may provide ameliorative effects with regard to inflammation, and can be beneficial in the treatment of diabetic neuropathy, and as such can be referred to as light having a therapeutic wavelength. The targeted body areas can include muscle, muscle groups, joints and human extremities, as examples. The garment 100 shown in FIGS. 1 and 2 is a long sleeve shirt and the garment 102 in FIG. 3 is a sock, however, the garment can be another type of garment, such as a short sleeve shirt, shorts, pants, gloves, etc. The garment 100 in FIGS. 1 and 2 is designed to be worn by a person in a similar manner as a conventional garment so that the long sleeve shirt would be worn over the upper body of a person, and in the case of socks (FIG. 3) worn over the feet and lower leg, for example.

Figure 4:
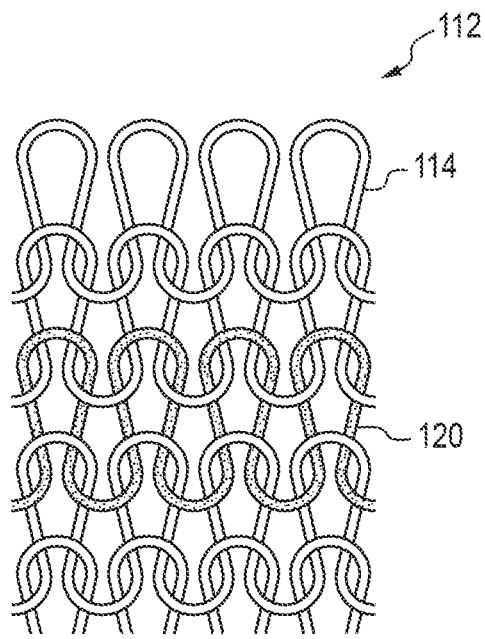
FIG. 4 is a schematic depiction of a knit pattern for a portion of the garment depicted in FIGS. 1-3.
Figure 5:
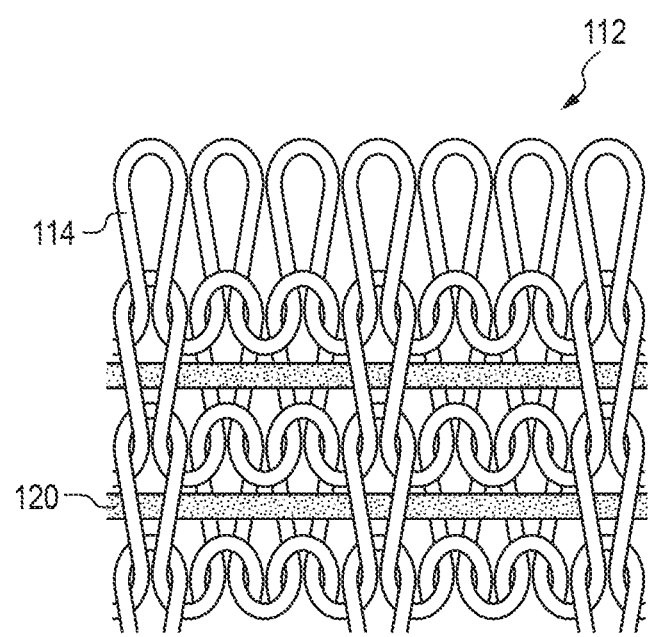
FIG. 5 is a schematic depiction of another knit pattern for a portion of the garment depicted in FIGS. 1-3.
Figure 6:
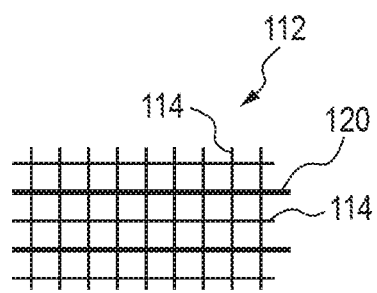
FIG. 6 is a schematic depiction of a woven pattern for a portion of the garment depicted in FIGS. 1-3.

With reference to FIGS. 4-6, each garment 100, 102 (FIGS. 1-3) includes a fabric base layer 112 formed from a yarn 114 or a plurality of yarns, which provides a comfort component for the garment. FIGS. 4 and 5 show examples of a knit fabric base layer 112. FIG. 6 shows an example of a woven fabric base layer 112. Examples of such yarn 114 can include cotton, polyester, cotton/polyester blends, microdenier polyester/cotton blends, and combinations thereof. It can be desirable to provide a skin-tight form-fitting garment to bring the therapeutic light source, which will be described in more detail below, very close to the wearer of the garment 100, 102. Accordingly, the yarn 114 can also include an elastic fiber such as lycra or spandex, and more than one type of yarn can form the fabric base layer 112.

The fabric base layer 112 can be made from fabric having a four way stretch, i.e., the fabric base layer 112 can have 100% or nearly 100% recovery along the grain and cross grain from 8% stretch. This can be desirable when the garment 100 is a shirt. The fabric base layer 112 can be made from fabric 100% or nearly 100% recovery along the grain and cross grain from 30% stretch, which can be useful when the garment 102 is a sock.

Knit fabrics can exhibit mechanical four way stretch, even without the use of elastic fibers, because of the manner in which the fabric is formed. Woven fabrics, in contrast, are typically not four way stretch fabrics, but instead stretch, if at all, along the bias, which is 45 degrees from the warp and weft yarns. Because woven fabrics typically do not stretch, fiber optic threads, which are not resilient, have been woven into fabrics in the weft, or filling direction. Woven fabrics, however, are not typically used to make skin-tight form-fitting garments that can be easily donned without the use of fasteners, such as buttons, snaps or hook and loop fasteners and other similar closures. Additionally, since knit fabrics loop each yarn in a relatively much smaller radius, as compared to the bend radius required for the warp yarns and weft yarns in a woven fabric, retaining or integrating fiber optic threads with a knitted fabric base layer is a difficult undertaking.

With reference back to FIGS. 2 and 3, each garment 100, 102 has an inner side 116 that faces towards a person's skin when wearing the garment and an outer side 118 that faces away from the person's skin when wearing the garment. Each garment 100, 102 also includes at least one side-emitting optical fiber 120 retained to or integrated with the fabric base layer 112, which is shown in FIGS. 4-6. A sufficient density of the side-emitting optical fiber 120 is located within at least one light-emitting zone 130, 132, 134, 136, 138 (see FIGS. 1 and 2) and 140 (see FIG. 3) that each are to be located over a targeted body area of the person wearing the garment 100, 102. The side-emitting optical fiber 120 receives light from a light source 122 (FIG. 7), which will be described in more detail below.

FIG. 4 depicts the fabric base layer 112 as a knit fabric base layer in which the side-emitting optical fiber 120 is incorporated as of one of the "yarns" to form the loops of the knit structure. FIG. 5 depicts the fabric base layer 112 as a knit fabric base layer in which the side-emitting optical fiber 120 is retained using an inlay technique. FIG. 6 depicts the fabric base layer 112 as a woven fabric base layer in which the side-emitting optical fiber 120 is integrated as a yarn in the filling direction; however, if desired the side-emitting optical fiber 120 can be integrated as a yarn in the warp direction. Unlike typical optical fibers, for example an optical fiber used to transmit light between two ends of the optical fiber in fiber-optic communications, at least within each of the light-emitting zones 130, 132, 134, 136, 138, 140, the side-emitting optical fiber 120 transmits light outwardly along the length of the side-emitting optical fiber 120. For example, the outer surface of the side-emitting optical fiber 120 can be etched, either mechanically or chemically, to allow light to escape the length of the side-emitting optical fiber 120. The side-emitting optical fiber 120 optically connects with the light source 122 (FIG. 7) located in an electronics module 142, which will be described in more detail below. Accordingly, in contrast to providing discrete LEDs, for example, embedded in the garment in each of the light-emitting zones, which can result in a garment that can be uncomfortable to wear, the light source can be remote and the at least one side-emitting optical fiber 120 can transmit the light from the light source 122 to each of the light-emitting zones 130, 132, 134, 136, 138, 140.

The garment 100 shown in FIGS. 1 and 2 depicts a left shoulder light-emitting zone 130, a right shoulder light-emitting zone 132, a lower back light-emitting zone 134, a left bicep light-emitting zone 136, and a right bicep light-emitting zone 138; however, other light-emitting zones can be provided especially where a different style of garment is provided. For example, in the case of the garment 102, which is a sock, the at least one light-emitting zone 140 is positioned to provide therapeutic light to the lower extremities of the wearer of the sock.

Figure 8:
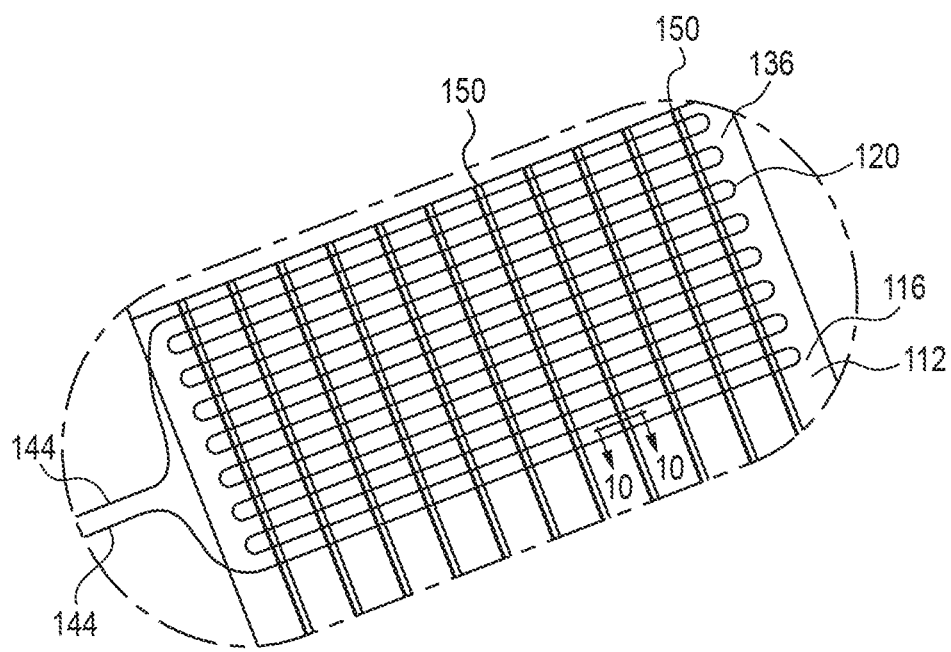
FIG. 8 depicts an inner side of the circled portion of the garment depicted in FIG. 2.

FIG. 8 depicts a portion of the inner side 116 of the garment 100 in the left bicep light-emitting zone 136 and an example of how the side-emitting optical fiber 120 is provided in the left bicep light-emitting zone 136. The side-emitting optical fiber 120 in the left bicep light-emitting zone 136 is configured to project light having a therapeutic wavelength toward the left bicep of the wearer of the garment 100. The side-emitting optical fiber 120 can be provided or situated similarly in the other light-emitting zones 130, 132, 134, 138 and 140 such that the side-emitting optical fiber 120 is configured to project light having a therapeutic wavelength toward the targeted body area covered by the respective light-emitting zone. As such, FIG. 8 will be referred to as exemplary for each of the light-emitting zones 130, 132, 134, 136, 138 and 140.

More particular to one embodiment, the light source 122 (FIG. 7) and the side-emitting optical fiber 120 located within in each light-emitting zone 130, 132, 134, 136, 138, 140 are configured to project light away from the inner side 116 of the garment 100, 102 having a wavelength between 630 nm and 900 nm. With reference to FIG. 8, the side-emitting optical fiber 120 is bent over itself in the light-emitting zone 136 and is provided in sufficient density within each light-emitting zone 130, 132, 134, 136, 138, 140 to provide a desired energy (Joules) of light at the therapeutic wavelength onto the targeted body area of the wearer of the garment 100, 102 based on the output wavelength and energy from the light source 122. Each row of the side-emitting optical fiber 120 can be spaced much more closely to one another than that shown in FIG. 8 to provide the desired energy of light to the targeted body area covered by the respective light-emitting zone 130, 132, 134, 136, 138, 140. By bending the side-emitting optical fiber 120 over itself in the light-emitting zone 130, 132, 134, 136, 138, instead of providing a plurality of side-emitting optical fibers that each terminate in a bundle that must be connected with a light source, fewer optical fiber tail sections 144 are needed to connect with the light source 122 to provide light to the respective light-emitting zone 130, 132, 134, 136, 138, 140 from the light source 122. FIG. 8 depicts two optical fiber tail sections 144 extending from the left bicep light-emitting zone 136. Having two optical fiber tail sections 144 that extend from the light-emitting zone 130, 132, 134, 136, 138, 140 to eventually connect the light source 122 provides a much smaller diameter element (or elements) that travels through generally non-illuminated areas of the garment 100, 102.

In the embodiment illustrated in FIG. 8, the side-emitting optical fiber 120 has a bend radius of less than 4 mm. More particularly, the side-emitting optical fiber 120 can have an outer diameter less than 0.5 mm and have a bend radius of less than 2.5 mm. In one embodiment, the side-emitting optical fiber 120 can have an outer diameter less than 0.25 mm have a bend radius of less than 1.25 mm. By comparison, the yarn 114 that provides the comfort component of the base layer can have an initial outer diameter of 0.375 mm, which decreases slightly to about 0.3 mm when knitted. Providing a relatively small diameter side-emitting optical fiber 120, for example as compared to a conventional optical fiber used in fiber-optic communications, and a side-emitting optical fiber 120 having such a small bend radius allows the garment 100, 102 to be comfortable while providing the appropriate wavelength of light at the appropriate energy to provide therapeutic effects to the wearer of the garment.

For the garment 100, 102 depicted in FIGS. 1-3, each light-emitting zone 130, 132, 134, 136, 138, 140 has a smaller area than that of the fabric base layer 112 such that the fabric base layer 112 at least partially surrounds each light-emitting zone so as to provide one (as depicted in FIG. 3) or a plurality (as depicted in FIGS. 1 and 2) of non-illuminated zones 146. As such, a comfortable garment 100, 102 having the fabric base layer 112 made of yarn 114, which provides a comfort component for the garment 100, 102, can be provided in areas of the garment other than in the light-emitting zones 130, 132, 134, 136, 138, 140, which can include the yarn 114 but also a higher concentration of the side-emitting optical fiber 120, which is not as bendable and stretchable as the yarn 114. In this manner, the garment 100, 102 can go from a relatively more comfortable and flexible zone or area in locations where the light-emitting zones 130, 132, 134, 136, 138, 140 are not provided to the light-emitting zones 130, 132, 134, 136, 138, 140 which include a relatively greater amount of side-emitting optical fiber 120, and back to the relatively more comfortable and flexible zone or area in locations where the light-emitting zones 130, 132, 134, 136, 138, 140 are not provided.

Figure 9:
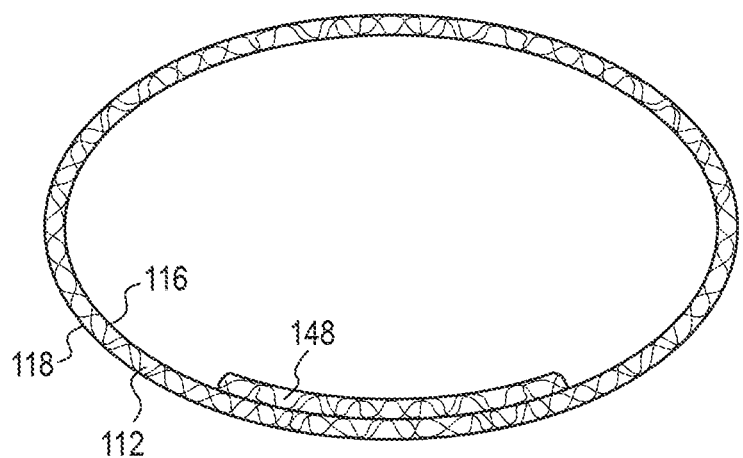
FIG. 9 is a cross-sectional view taken through line 9-9 in FIG. 2.

The side-emitting optical fiber 120 can be retained to or integrated with the fabric base layer 112 to provide the garment 100, 102 with a double or multiple layer construction in the light-emitting zones 130, 132, 134, 136, 138, 140. For example and with reference to FIG. 9, which shows the left bicep light-emitting zone 136 in cross section, the fabric base layer 112 can be an outer layer of the double or multiple layer construction and cover an inner layer 148, which includes the side-emitting optical fiber 120. The fabric base layer 112 can obscure light from the side-emitting optical fiber 120 from emanating outwardly away from the wearer of the garment 100 in each of the light-emitting zones 130, 132, 134, 136, 138. The side-emitting optical fiber 120 can be provided as part of the inner layer 148, with respect to the wearer's skin, of the double or multiple layer construction to position the side-emitting optical fiber 120 in contact with or in very close proximity to (e.g., within less than 1 mm) the wearer's skin. The garment 102 shown in FIG. 3 can have a similar double or multiple layer construction and look the same in cross section.

Figure 10:
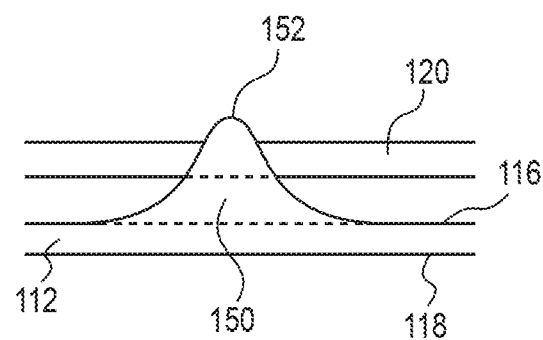
FIG. 10 is a cross-sectional view taken through line 10-10 in FIG. 8.

FIG. 5, for example, shows a particular example of a knitting technique that can be employed in each light-emitting zone 130, 132, 134, 136, 138, 140. FIG. 5 depicts a tunnel inlay knitting technique where the yarn 114 retains that side-emitting optical fiber 120 within each light-emitting zone 130, 132, 134, 136, 138, 140. With reference to FIGS. 8 and 10, the fabric base layer 112 can be knitted and include a plurality of loops 150 that hold in position the at least one side-emitting optical fiber 120 against or adjacent to the inner side 116 of fabric base layer 112. With reference to FIG. 10, each loop 150 has an apex 152 offset from the inner side 116 of the fabric base layer 112 a greater distance than a distance at which a farthest surface of the at least one side-emitting optical fiber 120 is offset from the inner side 116 of the fabric base layer 112. This can enhance the comfort of the garment 100, 102 by offsetting the side-emitting optical fiber 120 from the wearer's skin. With reference to FIG. 8, the plurality of loops 150 hold in position the at least one side-emitting optical fiber 120 and more than 90% of a total area of the at least one side-emitting optical fiber 120 facing toward the person's skin in each light-emitting zone 130, 132, 134, 136, 138, 140 is not covered by the plurality of loops 150 and is exposed to the person's skin. As such, the light directed toward the wearer's skin is only minimally obscured by the loops 150 retaining the side-emitting optical fiber 120 so as to increase the light energy being delivered to the wearer's skin.

With reference back to FIGS. 1-3, the fabric base layer 112 surrounds the light-emitting zones 130, 132, 134, 136, 138, 140 to provide the garment 100 with the at least one non-illuminated zone 160 where the light-emitting zones are not located. The fabric base layer 112 can be a single layer construction in each non-illuminated zone 160. As an example, the method of manufacture can involve first stitching the yarn 114, which can include an elastic fiber such as spandex or lycra, on a programmed knitting machine configured to produce a seamless garment 100, 102 to form a single layer construction fabric base layer 112. The garment 100, 102 can be provided with a seamless construction in that, for example, the garment 100 is not manufactured so as to have a front panel sewn to a back panel like a conventional shirt. The inner layer 148 (FIG. 9) is then retained to or integrated with the fabric base layer 112 to provide the garment 100, 102 with a double or multiple layer construction in the light-emitting zones 130, 132, 134, 136, 138, 140. As mentioned above, the side-emitting optical fiber 120 can be inlaid on the inner side 116 of the fabric base layer 112 (FIG. 8). The side-emitting optical fiber 120 can also be knitted onto the inner side 116 of the fabric base layer 112 to form the light-emitting zones 130, 132, 134, 136, 138, 140 using the programmed knitting machine to provide the inner layer 148 of the multiple layer construction.

Figure 11:
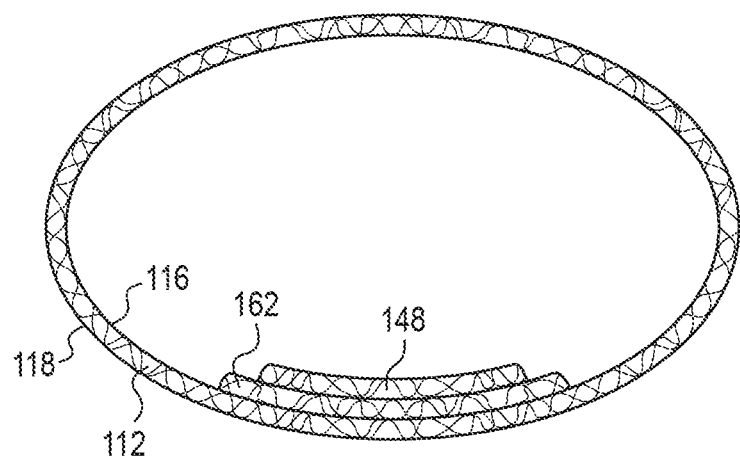
FIG. 11 is a cross-sectional view taken through line 11-11 in FIG. 2.

The garment 100, 102 can also include at least one reflective yarn retained to or integrated with the fabric base layer 112. The reflective yarn can be configured and located with respect to the side-emitting optical fiber 120 to reflect light emanating from the side-emitting optical fiber 120 toward a targeted body area of the wearer of the garment 100, 102. For example and even though it is not illustrated for each light-emitting zone 130, 132, 134, 136, 138, 140 the reflective yarn can be retained to or integrated with the fabric base layer 112 in each of the light-emitting zones 130, 132, 134, 136, 138, 140 and not be located in much of or any of non-illuminated zones 146. The reflective yarn can also be inlaid on the inner side 116 of the fabric base layer 112, or the reflective yarn can be knitted onto the inner side 116 of the fabric base layer 112 in the light-emitting zones 130, 132, 134, 136, 138, 140 using the programmed knitting machine to provide a reflective layer 162 in the multiple layer construction. If desired, the reflective yarn can extend beyond the light-emitting zones 130, 132, 134, 136, 138, 140. For example and with reference to FIG. 11, the reflective yarn can be located in the reflective layer 162, which surrounds and has a larger area than at least one light-emitting zone, which is the right bicep light-emitting zone 138 in the example illustrated in FIG. 2.

As mentioned above, the fabric base layer 112 can be made with yarn 114 including an elastic fiber to provide a stretchable fabric layer configured to conform to the person's skin when wearing the garment 100, 102. By forming the fabric base layer 112 as a stretchable fabric base layer, the fabric base layer retains the at least one side-emitting optical fiber 120 adjacent to or in contact with the person's skin when wearing the garment 100, 102. Accordingly, the at least one light-emitting zone 130, 132, 134, 136, 138, 140 is adjustable when the person is wearing the garment 100, 102 to modify a position of the at least one light-emitting zone 130, 132, 134, 136, 138, 140 with respect to the targeted body area of the person wearing the garment 100, 102. This allows the wearer of the garment 100, 102 to selectively locate each light-emitting zone 130, 132, 134, 136, 138, 140 in accordance with his or her preference. Also, the garment 100, 102 in each light-emitting zone 130, 132, 134, 136, 138, 140 maintains contact with the person's skin when wearing the garment 100, 102 even while the person is moving, e.g., bending his elbow, walking and the like.

The fabric base layer 112 can also be manufactured such that the garment 102 includes an elastic portion 164 having at least 8% stretch in at least one of the grain and cross grain direction. In the case of the garment 102, which is a sock in FIG. 3, providing the elastic portion 164 so as to have at least 30% stretch in both the grain and cross grain direction allows the sock to be easily donned as it is pulled over the heel. The remainder of the garment 102, i.e., the portion of the garment other than the elastic portion 164, need not have as much stretch. The elastic portion 164 for the garment 102 in FIG. 3 is located nearer to the upper end of the garment 102 as compared to the toes. Also in the case of the garment 102 depicted in FIG. 3, the sock can have a girth of up to 20 inches to accommodate persons of different size.

Figure 7:
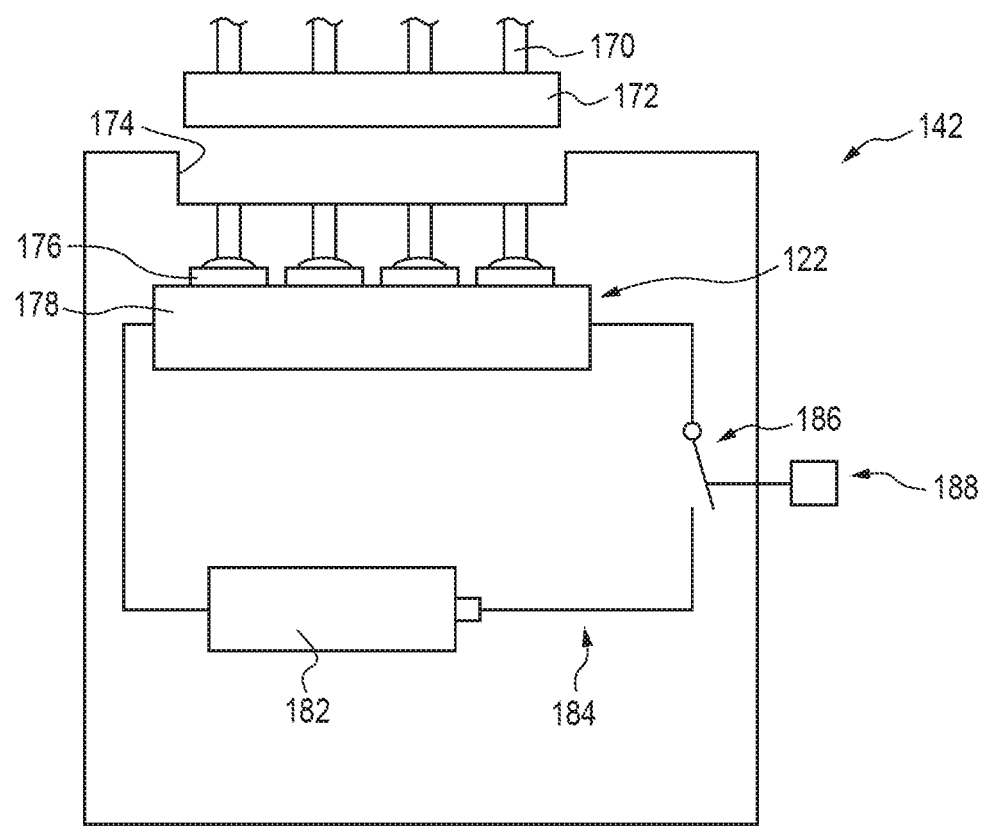
FIG. 7 is a schematic depiction of an electronics module for the garment depicted in FIGS. 1-3.

The light source 122 (FIG. 7) optically connects with the at least one side-emitting optical fiber 20. With reference to FIG. 7, when in use a proximal end 170 of the at least one side-emitting optical fiber 120 is positioned adjacent to the light source 122. FIG. 7 shows a plurality of side-emitting optical fibers 120 that terminate at a connector 172 that can be received in a socket 174 provided in the electronics module 142. With the connector 172 received in the socket 174, each proximal end 170 of each side-emitting optical fiber 120 is positioned with respect to the light source 122, which can include a plurality of LEDs 176 mounted on a circuit board 178, so that light emanating from each LED enters the appropriate side-emitting optical fiber 120. A distal end of each side-emitting optical fiber 120 can be provided with or covered by a reflective material, or each side-emitting optical fiber 120 can begin and end in the connector 172 so that both ends of each side-emitting optical fiber 120 can receive light from the light source 122. The electronics module 124 can also include a power source 182, such as a battery that can be disposable or rechargeable, electrically connected with the light source 122 through a circuit 184 including a switch 186. The switch 186 can be opened and closed using an actuator 188 to control power delivery to the light source 122.

It will be appreciated that various aspects of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A garment comprising:
   a fabric base layer having at least 8% stretch in the grain and cross grain direction of the fabric base layer; and
   at least one side-emitting optical fiber retained to or integrated with the fabric base layer, the at least one side-emitting optical fiber being located in at least one light-emitting zone to be located over a targeted body area of the person wearing the garment, wherein the at least one side-emitting optical fiber is configured to receive light from a light source and in the at least one light-emitting zone is configured to project light having a therapeutic wavelength toward the targeted body area,
   wherein the at least one side-emitting optical fiber is bent over itself in the at least one light-emitting zone and has only two optical fiber tail sections that extend from each light-emitting zone to eventually connect with the light source and both ends of the at least one side-emitting optical fiber receive light from the light source.

2. The garment of claim 1, wherein the fabric base layer has at least 30% stretch in the grain and cross grain direction.

3. The garment of claim 1, wherein the fabric base layer includes an elastic fiber having at least 99% recovery from 30% stretch.

4. The garment of claim 1, wherein the garment is a sock.

5. The garment of claim 4, wherein the sock has a girth up to 20 inches.

6. The garment of claim 1, wherein the at least one side-emitting optical fiber is retained to or integrated with the base layer to provide the garment with a double or multiple layer construction in the at least one light-emitting zone.

7. The garment of claim 1, wherein the base layer at least partially surrounds the at least one light-emitting zone to provide the garment with at least one non-illuminated zone where the at least one light-emitting zone is not located.

8. The garment of claim 7, wherein the base layer is a single layer construction in each non-illuminated zone.

9. The garment of claim 1, further comprising at least one reflective yarn retained to or integrated with the fabric base layer, wherein the reflective yarn is configured and located with respect to the at least one side-emitting optical fiber to reflect light emanating from the at least one side-emitting optical fiber toward the targeted body area.

10. The garment of claim 9, wherein the reflective yarn is located in at least one reflective layer that surrounds and has a larger area than the at least one light-emitting zone.

11. The garment of claim 6, wherein the garment has a double or multiple layer construction in the at least one reflective zone, the fabric base layer at least partially surrounds the reflective layer so as to provide the garment with at least one non-illuminated zone where the at least one illuminated zone is not located.

12. The garment of claim 1, wherein the fabric base layer is configured to conform to the person's skin when wearing the garment and the fabric base layer retains the at least one side-emitting optical fiber adjacent to or in contact with the person's skin when wearing the garment, and the at least one light-emitting zone is adjustable when the person is wearing the garment to modify a position of the at least one light-emitting zone with respect to the targeted body area of the person wearing the garment and maintain contact with the person's skin while moving.

13. The garment of claim 1, wherein the fabric base layer is a knit fabric base layer and includes a plurality of loops that hold in position the at least one side-emitting optical fiber against an inner side of the fabric base layer.

14. The garment of claim 13, wherein each loop has an apex offset from the inner side of the base layer a greater distance than a distance at which the least one side-emitting optical fiber is offset from the inner surface of the base layer.

15. The garment of claim 13, wherein more than 90% of a total area of the at least one side-emitting optical fiber facing toward the person's skin in the at least one light-emitting zone is not covered by the plurality of loops and is exposed to the person's skin.

16. The garment of claim 1, wherein the light source and the at least one side-emitting optical fiber located within the at least one light-emitting zone are configured to project light away from the inner side of the base layer having a wavelength between 630 nm and 900 nm.

17. The garment of claim 1, wherein the at least one side-emitting optical fiber has a bend radius of less than 4 mm.

18. The garment of claim 1, wherein the at least one side-emitting optical fiber has an outer diameter less than 1 mm and has a bend radius of less than 3 mm.

19. The garment of claim 1, wherein the at least one side-emitting optical fiber has an outer diameter less than 0.5 mm and a bend radius of less than 2.5 mm, and the fabric base layer includes yarn having a greater outer diameter than the at least one side-emitting optical fiber.

20. The garment of claim 1, wherein the fabric base layer is a knit seamless fabric base layer.

21. The garment of claim 20, wherein the fabric base layer includes a plurality of loops that hold in position the at least one side-emitting optical fiber in the at least one light-emitting zone and the at least one side-emitting optical fiber is inlaid against an inner side of base layer within the at least one light-emitting zone.

22. The garment of claim 21, wherein more than 90% of a total area of the at least one side-emitting optical fiber facing toward the person's skin in the at least one light-emitting zone is not covered by the plurality of loops and is exposed to the person's skin.

23. A garment comprising:
a knitted fabric base layer; and
at least one side-emitting optical fiber retained to or integrated with the fabric base layer, the at least one side-emitting optical fiber being located in at least one light-emitting zone to be located over a targeted body area of the person wearing the garment, wherein the at least one side-emitting optical fiber is configured to receive light from a light source and in the at least one light-emitting zone is configured to project light having a therapeutic wavelength toward the targeted body area,
wherein the base layer at least partially surrounds the at least one light-emitting zone to provide the garment with at least one non-illuminated zone where the at least one light-emitting zone is not located, and the at least one side-emitting optical fiber is bent over itself in the at least one light-emitting zone and has no more than two optical fiber tail sections that extend from each light-emitting zone through non-illuminated areas of the garment to eventually connect with the light source and both ends of the at least one side-emitting optical fiber receive light from the light source.

24. The garment of claim 23, wherein the fabric base layer has at least 8% stretch in the grain and cross grain direction.

25. The garment of claim 1, wherein the fabric base layer includes an elastic fiber having at least 99% recovery from 30% stretch.

26. The garment of claim 23, wherein the garment is a sock.

27. The garment of claim 26, wherein the sock has a girth up to 20 inches.

28. The garment of claim 23, wherein the at least one side-emitting optical fiber is retained to or integrated with the base layer to provide the garment with a double or multiple layer construction in the at least one light-emitting zone.

29. The garment of claim 23, wherein the base layer is a single layer construction in each non-illuminated zone.

30. The garment of claim 23, further comprising at least one reflective yarn retained to or integrated with the fabric base layer, wherein the reflective yarn is configured and located with respect to the at least one side-emitting optical fiber to reflect light emanating from the at least one side-emitting optical fiber toward the targeted body area.

31. The garment of claim 30, wherein the reflective yarn is located in at least one reflective layer that surrounds and has a larger area than the at least one light-emitting zone.

32. The garment of claim 30, wherein the garment has a double or multiple layer construction in the at least one reflective zone, the fabric base layer at least partially surrounds the reflective layer so as to provide the garment with at least one non-illuminated zone where the at least one illuminated zone is not located.

33. The garment of claim 23, wherein the fabric base layer is configured to conform to the person's skin when wearing the garment and the fabric base layer retains the at least one side-emitting optical fiber adjacent to or in contact with the person's skin when wearing the garment, and the at least one light-emitting zone is adjustable when the person is wearing the garment to modify a position of the at least one light-emitting zone with respect to the targeted body area of the person wearing the garment and maintain contact with the person's skin while moving.

34. The garment of claim 23, wherein the fabric base layer includes a plurality of loops that hold in position the at least one side-emitting optical fiber against an inner side of the fabric base layer.

35. The garment of claim 34, wherein each loop has an apex offset from the inner side of the base layer a greater distance than a distance at which the least one side-emitting optical fiber is offset from the inner surface of the base layer.

36. The garment of claim 34, wherein more than 90% of a total area of the at least one side-emitting optical fiber facing toward the person's skin in the at least one light-emitting zone is not covered by the plurality of loops and is exposed to the person's skin.

37. The garment of claim 23, wherein the light source and the at least one side-emitting optical fiber located within the at least one light-emitting zone are configured to project light away from the inner side of the base layer having a wavelength between 630 nm and 900 nm.

38. The garment of claim 23, wherein the at least one side-emitting optical fiber has a bend radius of less than 4 mm.

39. The garment of claim 23, wherein the at least one side-emitting optical fiber has an outer diameter less than 1 mm and has a bend radius of less than 3 mm.

40. The garment of claim 23, wherein the at least one side-emitting optical fiber has an outer diameter less than 0.5 mm and a bend radius of less than 2.5 mm, and the fabric base layer includes yarn having a greater outer diameter than the at least one side-emitting optical fiber.

41. The garment of claim 23, wherein the fabric base layer is a knit seamless fabric base layer.

42. The garment of claim 41, wherein the fabric base layer includes a plurality of loops that hold in position the at least one side-emitting optical fiber in the at least one light-emitting zone and the at least one side-emitting optical fiber is inlaid against an inner side of base layer within the at least one light-emitting zone.

43. The garment of claim 41, wherein more than 90% of a total area of the at least one side-emitting optical fiber facing toward the person's skin in the at least one light-emitting zone is not covered by the plurality of loops and is exposed to the person's skin.

44. A therapeutic sock comprising:
a fabric base layer including an elastic fiber in at least an elastic portion of the sock, the elastic portion having at least 8% stretch in the grain and cross grain direction; and at least one side-emitting optical fiber retained to or integrated with the fabric base layer, the at least one side-emitting optical fiber being located in at least one light-emitting zone to be located over a targeted body area of the person wearing the sock, wherein the at least one side-emitting optical fiber is configured to receive light from a light source and in the at least one light-emitting zone is configured to project light having a therapeutic wavelength toward the targeted body area, wherein the at least one side-emitting optical fiber is bent over itself in the at least one light-emitting zone and has only two optical fiber tail sections that extend from each light-emitting zone to eventually connect with the light source and both ends of the at least one side-emitting optical fiber receive light from the light source.

45. The therapeutic sock of claim 44, wherein the elastic portion has at least 30% stretch in the grain and cross grain direction.

46. The therapeutic sock of claim 44, wherein the elastic fiber has at least 99% recovery from 30% stretch.

47. The therapeutic sock of claim 44, wherein the sock has a girth up to 20 inches.

48. The therapeutic sock of claim 44, wherein the at least one side-emitting optical fiber is retained to or integrated with the base layer to provide the therapeutic sock with a double or multiple layer construction in the at least one light-emitting zone.

49. The therapeutic sock of claim 44, wherein the fabric base layer includes at least one non-illuminated zone where the at least one light-emitting zone is not located, and the fabric base layer is a single layer construction in each non-illuminated zone.

50. The therapeutic sock of claim 44, further comprising at least one reflective yarn retained to or integrated with the fabric base layer, wherein the reflective yarn is configured and located with respect to the at least one side-emitting optical fiber to reflect light emanating from the at least one side-emitting optical fiber toward the targeted body area.

51. The therapeutic sock of claim 50, wherein the reflective yarn is located in at least one reflective layer that surrounds and has a larger area than the at least one light-emitting zone.

52. The therapeutic sock of claim 44, wherein the fabric base layer is configured to conform to the person's skin when wearing the therapeutic sock and the fabric base layer retains the at least one side-emitting optical fiber adjacent to or in contact with the person's skin when wearing the therapeutic sock, and the at least one light-emitting zone is adjustable when the person is wearing the therapeutic sock to modify a position of the at least one light-emitting zone with respect to the targeted body area of the person wearing the therapeutic sock and maintain contact with the person's skin while moving.

53. The therapeutic sock of claim 44, wherein the fabric base layer is a knit fabric base layer and includes a plurality of loops that hold in position the at least one side-emitting optical fiber against an inner side of the fabric base layer.

54. The therapeutic sock of claim 53, wherein each loop has an apex offset from the inner side of the base layer a greater distance than a distance at which the least one side-emitting optical fiber is offset from the inner surface of the base layer.

55. The therapeutic sock of claim 53, wherein more than 90% of a total area of the at least one side-emitting optical fiber facing toward the person's skin in the at least one light-emitting zone is not covered by the plurality of loops and is exposed to the person's skin.

56. The therapeutic sock of claim 44, wherein the light source and the at least one side-emitting optical fiber located within the at least one light-emitting zone are configured to project light away from the inner side of the base layer having a wavelength between 630 nm and 900 nm.

57. The therapeutic sock of claim 44, wherein the at least one side-emitting optical fiber has a bend radius of less than 4 mm.

58. The therapeutic sock of claim 44, wherein the at least one side-emitting optical fiber has an outer diameter less than 1 mm and has a bend radius of less than 3 mm.

59. The therapeutic sock of claim 44, wherein the at least one side-emitting optical fiber has an outer diameter less than 0.5 mm and a bend radius of less than 2.5 mm, and the fabric base layer includes yarn having an outer diameter greater than the at least one side-emitting optical fiber.

60. The therapeutic sock of claim 44, wherein the fabric base layer is a knit seamless fabric base layer.

61. The therapeutic sock of claim 60, wherein the fabric base layer includes a plurality of loops that hold in position the at least one side-emitting optical fiber in the at least one light-emitting zone and the at least one side-emitting optical fiber is inlaid against an inner side of base layer within the at least one light-emitting zone.

62. The therapeutic sock of claim 60, wherein more than 90% of a total area of the at least one side-emitting optical fiber facing toward the person's skin in the at least one light-emitting zone is not covered by the plurality of loops and is exposed to the person's skin.

63. A garment comprising a fabric base layer and at least one side-emitting optical fiber retained to or integrated with the fabric base layer, the fabric base layer is configured to conform to the person's skin when wearing the garment and the fabric base layer retains the at least one side-emitting optical fiber adjacent to or in contact with the person's skin when wearing the garment, the at least one side-emitting optical fiber being located in at least one light-emitting zone to be located over a targeted body area of the person wearing the garment, the at least one side-emitting optical fiber is configured to receive light from a light source and in the at least one light-emitting zone is configured to project light having a therapeutic wavelength toward the targeted body area, and the at least one light-emitting zone is adjustable when the person is wearing the garment to modify a position of the at least one light-emitting zone with respect to the targeted body area of the person wearing the garment and maintain contact with the person's skin while the person wearing the garment is moving, wherein the at least one side-emitting optical fiber is bent over itself in the at least one light-emitting zone and has only two optical fiber tail sections that extend from each light-emitting zone to eventually connect with the light source and both ends of the at least one side-emitting optical fiber receive light from the light source.

64. The garment of claim 63, wherein the fabric base layer has at least 8% stretch in the grain and cross grain direction.

65. The garment of claim 63, wherein the fabric base layer includes an elastic fiber having at least 99% recovery from 30% stretch.

66. The garment of claim 63, wherein the garment is a sock.

67. The garment of claim 66, wherein the sock has a girth up to 20 inches.

68. The garment of claim 63, wherein the at least one side-emitting optical fiber is retained to or integrated with the base layer to provide the garment with a double or multiple layer construction in the at least one light-emitting zone.

69. The garment of claim 63, wherein the fabric base layer at least partially surrounds the at least one light-emitting zone to provide the garment with at least one non-illuminated zone where the at least one light-emitting zone is not located.

70. The garment of claim 69, wherein the base layer is a single layer construction in each non-illuminated zone.

71. The garment of claim 63, further comprising at least one reflective yarn retained to or integrated with the fabric base layer, wherein the reflective yarn is configured and located with respect to the at least one side-emitting optical fiber to reflect light emanating from the at least one side-emitting optical fiber toward the targeted body area.

72. The garment of claim 71, wherein the reflective yarn is located in at least one reflective layer that surrounds and has a larger area than the at least one light-emitting zone.

73. The garment of claim 72, wherein the garment has a double or multiple layer construction in the at least one reflective layer, the fabric base layer at least partially surrounds the reflective layer so as to provide the garment with at least one non-illuminated zone where the at least one illuminated zone is not located.

74. The garment of claim 63, wherein the fabric base layer includes a plurality of loops that hold in position the at least one side-emitting optical fiber against an inner side of the fabric base layer.

75. The garment of claim 74, wherein each loop has an apex offset from the inner side of the base layer a greater distance than a distance at which the least one side-emitting optical fiber is offset from the inner surface of the base layer.

76. The garment of claim 74, wherein more than 90% of a total area of the at least one side-emitting optical fiber facing toward the person's skin in the at least one light-emitting zone is not covered by the plurality of loops and is exposed to the person's skin.

77. The garment of claim 63, wherein the light source is optically connected with the at least one side-emitting optical fiber, wherein the light source and the at least one side-emitting optical fiber located within the at least one light-emitting zone are configured to project light away from the inner side of the base layer having a wavelength between 630 nm and 900 nm.

78. The garment of claim 63, wherein the at least one side-emitting optical fiber has a bend radius of less than 4 mm.

79. The garment of claim 63, wherein the at least one side-emitting optical fiber has an outer diameter less than 1 mm and has a bend radius of less than 3 mm.

80. The garment of claim 63, wherein the at least one side-emitting optical fiber has an outer diameter less than 0.5 mm and a bend radius of less than 2.5 mm, and the fabric base layer includes yarn having an outer diameter greater than the at least one side-emitting optical fiber.

81. The garment of claim 63, wherein the fabric base layer is a knit seamless fabric base layer.

82. The garment of claim 81, wherein the fabric base layer includes a plurality of loops that hold in position the at least one side-emitting optical fiber in the at least one light-emitting zone and the at least one side-emitting optical fiber is inlaid against an inner side of base layer within the at least one light-emitting zone.

83. The garment of claim 81, wherein more than 90% of a total area of the at least one side-emitting optical fiber facing toward the person's skin in the at least one light-emitting zone is not covered by the plurality of loops and is exposed to the person's skin.

\* \* \* \* \*